(12) United States Patent
Kuo et al.

(10) Patent No.: US 9,649,622 B1
(45) Date of Patent: May 16, 2017

(54) BIMETAL OXYSULFIDE SOLID-SOLUTION CATALYST AND MANUFACTURING METHOD THEREOF, METHOD FOR CARBON DIOXIDE REDUCTION, METHOD FOR HEAVY METAL REDUCTION, AND METHOD FOR HYDROGENATION OF ORGANIC COMPOUNDS

(71) Applicant: National Taiwan University of Science and Technology, Taipei (TW)

(72) Inventors: Dong-Hau Kuo, Taipei (TW); Xiaoyun Chen, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 0 days.

(21) Appl. No.: 15/155,651

(22) Filed: May 16, 2016

(51) Int. Cl.
| | | |
|---|---|---|
| *B01J 27/02* | (2006.01) | |
| *B01J 37/04* | (2006.01) | |
| *B01J 37/03* | (2006.01) | |
| *B01J 37/00* | (2006.01) | |
| *B01J 37/02* | (2006.01) | |
| *B01D 53/86* | (2006.01) | |
| *C07D 311/82* | (2006.01) | |
| *C07C 309/45* | (2006.01) | |
| *C07D 279/20* | (2006.01) | |
| *A62D 3/37* | (2007.01) | |
| *A62D 101/43* | (2007.01) | |

(52) U.S. Cl.
CPC ............. *B01J 27/02* (2013.01); *A62D 3/37* (2013.01); *B01D 53/8671* (2013.01); *B01J 37/009* (2013.01); *B01J 37/0236* (2013.01); *B01J 37/031* (2013.01); *B01J 37/04* (2013.01); *C07C 309/45* (2013.01); *C07D 279/20* (2013.01); *C07D 311/82* (2013.01); *A62D 2101/43* (2013.01); *B01D 2255/2098* (2013.01); *B01D 2255/20761* (2013.01); *B01D 2255/20769* (2013.01); *B01D 2255/20792* (2013.01); *B01D 2257/504* (2013.01)

(58) Field of Classification Search
CPC ...... B01J 27/02; B01J 37/009; B01J 37/0236; B01J 37/031; B01J 37/04; B01D 53/8671; B01D 2255/20761; B01D 2255/20769; B01D 2255/20792; B01D 2255/2098; B01D 2257/504; C07C 309/45; C07D 279/20; C07D 311/82
USPC .................................................. 502/216, 220
See application file for complete search history.

(56) References Cited

U.S. PATENT DOCUMENTS

| | | | | |
|---|---|---|---|---|
| 5,122,357 A | * | 6/1992 | Bedard | ................... B01J 29/005 210/767 |
| 5,594,263 A | * | 1/1997 | Bedard | ............... H01L 51/4233 257/201 |
| 2004/0029726 A1 | * | 2/2004 | Domen | .................... B01J 27/04 502/216 |

FOREIGN PATENT DOCUMENTS

WO 87/06138 * 10/1987 ............ A61K 43/00

* cited by examiner

*Primary Examiner* — Patricia L Hailey
(74) *Attorney, Agent, or Firm* — J.C. Patents

(57) ABSTRACT

A bimetal oxysulfide solid-solution catalyst is provided. The bimetal oxysulfide solid-solution catalyst is represented by formula (1):

$$M^{(1)}_x M^{(2)}_y O_z S_\gamma \qquad (1),$$

wherein in formula (1), $M^{(1)}$ includes Copper (Cu) and $M^{(2)}$ includes monovalent Silver (Ag), divalent Zinc (Zn), Manganese (Mn), Nickel (Ni), Cobalt (Co), and Tin ($Sn^{II}$), trivalent Indium (In), Cerium (Ce), Antimony (Sb), and Gallium (Ga), tetravalent Tin ($Sn^{IV}$), or pentavalent Molybdenum (Mo), $0<y<0.3$, $0.7<x<1.0$, $0<z<0.5$, and $0.5<\gamma<1.0$. In addition, a manufacturing method of the bimetal oxysulfide solid-solution catalyst and applications of the bimetal oxysulfide solid-solution catalyst are also provided.

11 Claims, No Drawings

BIMETAL OXYSULFIDE SOLID-SOLUTION CATALYST AND MANUFACTURING METHOD THEREOF, METHOD FOR CARBON DIOXIDE REDUCTION, METHOD FOR HEAVY METAL REDUCTION, AND METHOD FOR HYDROGENATION OF ORGANIC COMPOUNDS

BACKGROUND OF THE INVENTION

1. Field of the Invention

The present invention generally relates to a catalyst, a manufacturing method of the catalyst, a method of carbon dioxide (CO2) reduction using the catalyst, a method of heavy metal reduction using the catalyst, and a method of hydrogenation of organic compounds. In particular, the present invention relates to an oxysulfide catalyst including copper.

2. Description of Related Art

Recently, global warming and climate change has become a huge threat to the environment. Therefore, $CO_2$ emission is an important issue awaiting to be solved worldwide. In particular, a method of converting $CO_2$ into methanol ($CH_3OH$) using ruthenium (Ru) metal complex has been proposed. However, such mechanism requires external energy, such as external high power light sources, to trigger the reaction. Therefore, it is difficult to conduct the conversion at room temperature and atmosphere pressure. High power light sources not only impose a burden on the cost of the conversion, but also raise safety issues on a scale-up production system. Therefore, providing catalyst which enables elimination of $CO_2$ while being cost effective has become a topic to be researched in the field.

One of the heavy metal ions with highly toxic property is hexavalent chromium (Cr(VI)) which is widely used in industrial activities such as plastic, leather, textile, metal, electroplating processing, etc. The existence of Cr(VI) in drinking water has engrossed the attention of many scientists to remediate it due to its poisonous property and adverse effect on drinking water. The highly mobile nature and non biodegradability of Cr(VI) are not only harmful to aqueous environment but also to human life. Therefore, the reduction of Cr(VI) is highly required for environmental remediation.

Hydrogenation of organic compounds involves in many chemical reactions to facilitate the formation of second compound. The hydrogenation reaction has been popular to undergo with the hydrogen gas flow and catalyst of Pt, Pd, Ni, etc. High temperature is needed for the $H_2$-involving reaction. The reduction reaction at mild condition for a green and safe synthesis is encouraging.

SUMMARY OF THE INVENTION

The invention provides a catalyst and a manufacturing thereof, which effectively aids the conversion of $CO_2$ gas into methanol, effectively aids the reduction of heavy metal, or effectively aids the hydrogenation of organic compounds at atmospheric condition.

The invention provides a bimetal oxysulfide solid-solution catalyst. The catalyst is represented by formula (1):

$$M^{(1)}_x M^{(2)}_y O_z S_\gamma \quad (1),$$

wherein in formula (1), $M^{(1)}$ includes a multivalent metal and $M^{(2)}$ includes a mono-, di-, tri-, tetra-, or penta-valent metal; $0<y<0.3$; $0.7<x<1.0$; $0<z<0.5$; $0.5<\gamma<1.0$.

In an embodiment of the invention, $M^{(1)}$ includes Copper (Cu) and the bimetal oxysulfide solid-solution catalyst is represented by formula (2):

$$Cu_x M^{(2)}_y O_z S_\gamma \quad (2),$$

wherein in formula (2), $M^{(2)}$ comprises the mono-, di-, tri-, tetra-, or penta-valent metal; $0<y<0.3$; $0.7<x<1.0$; $0<z<0.5$; $0.5<y<1.0$.

In an embodiment of the invention, in formula (2), $M^{(2)}$ includes monovalent Silver (Ag), divalent Zinc (Zn), Manganese (Mn), Nickel (Ni), Cobalt (Co), and Tin ($Sn^{II}$), trivalent Indium (In), Cerium (Ce), Antimony (Sb), and Gallium (Ga), tetravalent Tin ($Sn^{IV}$), or pentavalent Molybdenum (Mo).

The invention provides a manufacturing method of the bimetal oxysulfide solid-solution catalyst. First, a copper-containing salt is dissolved in distilled water to obtain a first solution. Meanwhile, an $M^{(2)}$-containing compound is dissolved in distilled water to obtain a second solution. The first solution and the second solution are mixed to obtain a mixture solution. An organosulfur compound is added into the mixture solution, and the mixture solution is heated to a temperature range of 50-100° C. A precipitate is centrifuged from the mixture solution and is dried to obtain the bimetal oxysulfide solid-solution catalyst.

In an embodiment of the invention, the method further includes a step of adding hydrazine to the mixture solution in a dropwise manner.

The invention provides a method for $CO_2$ reduction. First, the bimetal oxysulfide solid-solution catalyst and a reactant solution are provided in the reactor. Subsequently, $CO_2$ gas is passed into the reactor to react with the reactant solution.

The invention provides a method for heavy metal reduction. First, the bimetal oxysulfide solid-solution catalyst is provided in a reactor. Then, a heavy metal aqueous solution is added to the reactor. Subsequently, the bimetal oxysulfide solid-solution catalyst and the heavy metal aqueous solution are reacted.

In an embodiment of the invention, the heavy metal includes hexavalent chromium (Cr(VI)).

The invention provides a method for the hydrogenation of organic compounds at an atmospheric condition. First, the bimetal oxysulfide solid-solution catalyst, an aqueous solution of organic compounds, and a reducing agent are added to a reactor. Subsequently, the bimetal oxysulfide solid-solution catalyst and the organic aqueous solution are reacted.

In an embodiment of the invention, the compounds includes rhodamine B, methyl orange, or methylene blue.

In an embodiment of the invention, the reducing agent includes sodium boron hydride or oxalic acid.

Based on the above, the bimetal oxysulfide solid-solution catalyst of the invention includes copper element and may be manufactured at a low temperature. Due to the specific structure of the catalyst of the invention, $CO_2$ gas may be converted to methanol and reduction of heavy metal and the hydrogenation of organic chemicals may be performed at atmospheric condition. As such, the power requirement for external energy may be eliminated. In addition, the bimetal oxysulfide solid-solution catalyst of the invention may be recycled. Therefore, the cost for the reduction processes may be significantly lowered.

DESCRIPTION OF THE EMBODIMENTS

Reference will now be made in detail to the present preferred embodiments of the invention, examples of which are illustrated in the accompanying drawings. Wherever possible, the same reference numbers are used in the drawings and the description to refer to the same or like parts.

A bimetal oxysulfide solid-solution catalyst is prepared at a low temperature condition. Specifically, 4.6 grams of a $M^{(1)}$-containing salt is dissolved in distilled water to obtain a first solution. Meanwhile, 2 grams to 6 grams of an $M^{(2)}$-containing compound is dissolved in 250 mL of distilled water to obtain a second solution. $M^{(1)}$ is a multivalent metal. For example, $M^{(1)}$ may be copper and the $M^{(1)}$-containing salt may be copper nitrate. However, it construes no limitation in the invention. Other suitable copper-containing salt may be used as well. On the other hand, $M^{(2)}$ is, for example, mono-, di-, tri-, tetra-, or penta-valent metal. Specific examples of $M^{(2)}$ includes, but not limited to, monovalent Silver (Ag), divalent Zinc (Zn), Manganese (Mn), Nickel (Ni), Cobalt (Co), and Tin ($Sn^{II}$), trivalent Indium (In), Cerium (Ce), Antimony (Sb), and Gallium (Ga), tetravalent Tin ($Sn^{IV}$), pentavalent Molybdenum (Mo), or other similar metal elements. In other words, examples of the $M^{(2)}$-containing compound may include zinc acetate dihydrate, manganese (II) chloride, cobalt (II) chloride, nickel (II) chloride, indium (III) chloride, tin (II) chloride, cerium (III) nitrate hexahydrate, antimony (III) chloride, gallium (III) acetate, tin (IV) chloride hydrate, molybdenum (V) chloride, silver (I) nitrate, or other metal salts. However, they construe no limitation in the disclosure. Other compounds including suitable metal compounds may also be adapted. Subsequently, the first solution and the second solution are mixed while being stirred by a magnet for 30 minutes to obtain a mixture solution. An organosulfur compound having a concentration of 15 g/L is added into the mixture solution and the mixture solution is allowed to react with the organosulfur compound for 30 minutes. The organosulfur compound is, for example, thioacetamide or other suitable compound. Subsequently, the mixture solution is heated to a temperature range of 50° C. to 100° C. and 0.15 mL of hydrazine is added to the mixture solution in a dropwise manner to react for 2 hours. Thereafter, the precipitate is centrifuged. After rinsing the precipitate with distilled water until the precipitate is neutral, the precipitate is further rinsed twice with absolute ethanol. The precipitate is dried by an evaporator to obtain a bimetal oxysulfide solid-solution catalyst.

The bimetal oxysulfide solid-solution catalyst obtained is represented by formula (1):

$$M^{(1)}_x M^{(2)}_y O_z S_\gamma \quad (1),$$

in formula (1), $M^{(1)}$ includes Copper (Cu) and $M^{(2)}$ includes monovalent Silver (Ag), divalent Zinc (Zn), Manganese (Mn), Nickel (Ni), Cobalt (Co), and Tin ($Sn^{II}$), trivalent Indium (In), Cerium (Ce), Antimony (Sb), and Gallium (Ga), tetravalent Tin ($Sn^{IV}$), or pentavalent Molybdenum (Mo), $0<y<0.3$, $0.7<x<1.0$, $0<z<0.5$, and $0.5<\gamma<1.0$.

The bimetal oxysulfide solid-solution catalyst obtained may have various applications. For example, the bimetal oxysulfide solid-solution catalyst may be used for $CO_2$ reduction, heavy metal reduction, or hydrogenation of organic compounds.

Specifically, when the bimetal oxysulfide solid-solution catalyst is used for $CO_2$ reduction, 0.1 gram of catalyst is provided in a reactor. Subsequently, 100 mL of reactant solution is added to the reactor. The reactant solution is, for example, a solution includes water. The reactant solution and the bimetal oxysulfide solid-solution catalyst are being stirred with a magnet with a stirring speed of 280 rpm (revolutions per minute). Thereafter, $CO_2$ gas is passed into the reactor to react with the reactant solution. In the present embodiment, the $CO_2$ gas may be generated by decomposing sodium bicarbonate ($NaHCO_3$) with the droplet addition of diluted nitric acid ($HNO_3$) aqueous solution to control the $CO_2$ generation. However, it construes no limitation in the invention. Other alternative $CO_2$ gas source may be adapted. The $CO_2$ gas is allowed to react with the reactant solution for 16-24 hours to generate methanol. In other words, the bimetal oxysulfide solid-solution catalyst of the present embodiment aids the conversion of $CO_2$ gas into methanol. It should be noted that the foregoing process is conducted at atmospheric condition. In other words, the process is performed at room temperature under atmosphere pressure. Alternatively speaking, only ambient light is present and no additional energy source is required. However, the invention is not limited thereto. In some other alternative embodiments, the reaction may be conducted in a dark room. That is, the reaction may be performed without the presence of any external energy.

In some alternative embodiments, the bimetal oxysulfide solid-solution catalyst of the invention may be used for heavy metal reduction. Specifically, when the bimetal oxysulfide solid-solution catalyst is used for heavy metal reduction, 0.1 grams of the bimetal oxysulfide solid-solution catalyst is provided in a reactor. Subsequently, 100 mL of a heavy metal aqueous solution with a concentration of 50 ppm is added into the reactor. The heavy metal is, for example, metallic element having an atomic number of 20 or greater. In the present embodiment, the heavy metal may include environment harmful hexavalent chromium (Cr (VI)). However, it construes no limitation in the invention. Other heavy metals may also be the subject for reduction. Thereafter, shake the reactor to render a uniform distribution of the bimetal oxysulfide solid-solution catalyst in the heavy metal aqueous solution. The bimetal oxysulfide solid-solution catalyst and the heavy metal aqueous solution are allowed to react for 2 minutes, so as to perform heavy metal reduction.

In some alternative embodiments, the bimetal oxysulfide solid-solution catalyst may be recycled. For example, after the foregoing heavy metal reduction process, the bimetal oxysulfide solid-solution catalyst may be centrifuged to separate from the solution. Without rinsing the bimetal oxysulfide solid-solution catalyst, the foregoing step of heavy metal reduction may be repeated again.

In some alternative embodiments, the bimetal oxysulfide solid-solution catalyst of the invention may be used for the hydrogenation of organic compounds. Specifically, when the bimetal oxysulfide solid-solution catalyst is used for hydrogenation reaction, 100 mL of aqueous solution of organic compounds (a dye aqueous solution) with a concentration of 100 ppm is add into in a 250 mL conical flask. Subsequently, 5 mL of reducing agent aqueous solution with a concentration of 0.1 mole is added into the conical flask. The organic compound is, for example, hydrocarbon having double or triple bonds. In the present embodiment, the organic compound may include methylene blue, methylene orange, or rhodamine B. However, it construes no limitation in the invention. Other organic compounds may also be the subject for hydrogenation reaction. On the other hand, the reducing agent is, for example, sodium boron hydride or oxalic acid. Under the stirring condition, 0.01 gams of the bimetal oxysulfide solid-solution catalyst is provided in the conical flask. Thereafter, shake the conical flask to render a uniform distribution of the bimetal oxysulfide solid-solution catalyst in the dye aqueous solution. The bimetal oxysulfide solid-solution catalyst and the dye aqueous solution are allowed to react for hydrogenation reaction.

The examples of the invention will be described in detail below.

Synthesis Example 1

Copper Zinc Oxysulfide ($Cu_xZn_yO_zS_y$) Powder 1

4.6 grams of copper nitrate ($Cu(NO_3)_2 \cdot 2.5H_2O$) is dissolved in 250 mL of distilled water to obtain a first solution. 6.0 grams of zinc acetate dihydrate ($Zn(CH_3COO)_2 \cdot 2H_2O$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 1.

Synthesis Example 2

Copper Manganese Oxysulfide ($Cu_xMn_yO_zS_y$) Powder 2

4.6 grams of copper nitrate ($Cu(NO_3)_2$-$2.5H_2O$) is dissolved in 250 mL of distilled water to obtain a first solution. 2.0 grams of manganese (II) chloride ($MnCl_2$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 2.

Synthesis Example 3

Copper Cobalt Oxysulfide ($Cu_xCo_yO_zS_y$) Powder 3

4.6 grams of copper nitrate ($Cu(NO_3)_2 \cdot 2.5H_2O$) is dissolved in 250 mL of distilled water to obtain a first solution. 3.0 grams of cobalt (II) chloride ($CoCl_2$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 3.

Synthesis Example 4

Copper Nickel Oxysulfide ($Cu_xNi_yO_zS_y$) Powder 4

4.6 grains of copper nitrate ($Cu(NO_3)_2 \cdot 2.5H_2O$) is dissolved in 250 mL of distilled water to obtain a first solution. 3.0 grams of nickel (II) chloride ($NiCl_2$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 4.

Synthesis Example 5

Copper Indium Oxysulfide ($Cu_xIn_yO_zS_7$) Powder 5

4.6 grams of copper nitrate ($Cu(NO_3)_2 \cdot 2.5H_2O$) is dissolved in 250 mL of distilled water to obtain a first solution. 3.0 grams of indium (III) chloride ($InCl_3$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 5.

Synthesis Example 6

Copper Tin (II) Oxysulfide ($Cu_xSn^{II}_yO_zS_y$) Powder 6

4.6 grams of copper nitrate ($Cu(NO_3)_2 \cdot 2.5H_2O$) is dissolved in 250 mL of distilled water to obtain a first solution. 3.0 grams of anhydrous tin (II) chloride ($SnCl_2$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged.

After rinsing the precipitate with distilled water until the precipitate is neutral, the precipitate is further rinsed twice with absolute ethanol. The precipitate is dried by an evaporator to obtain powder 6.

Synthesis Example 7

Copper Cerium Oxysulfide ($Cu_xCe_yO_zS_\gamma$) Powder 7

4.6 grams of copper nitrate ($Cu(NO_3)_2.2.5H_2O$) is dissolved in 250 mL of distilled water to obtain a first solution. 4.64 grams of cerium (III) nitrate hexahydrate ($Ce(NO_2)_3.6H_2O$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 85 t and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 7.

Synthesis Example 8

Copper Antimony Oxysulfide ($Cu_xSb_yO_zS_\gamma$) Powder 8

4.6 grams of copper nitrate ($Cu(NO_3)_2.2.5H_2O$) is dissolved in 250 mL of distilled water to obtain a first solution. 3.0 grams of antimony (III) chloride ($SbCl_3$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 8.

Synthesis Example 9

Copper Gallium Oxysulfide ($Cu_xGa_yO_zS_\gamma$) Powder 9

4.6 grams of copper nitrate ($Cu(NO_3)_2.2.5H_2O$) is dissolved in 250 mL of distilled water to obtain a first solution. 3.0 grams of gallium (III) acetate ($Ga(CH_3COO)_3$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 95° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 9.

Synthesis Example 10

Copper Tin (IV) Oxysulfide ($Cu_xSn^{IV}_yO_zS_\gamma$) Powder 10

4.6 grams of copper nitrate ($Cu(NO_3)_2.2.5H_2O$) is dissolved in 250 mL of distilled water to obtain a first solution. 4.0 grams of tin (IV) chloride hydrate ($SnCl_4.xH_2O$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol.

The precipitate is dried by an evaporator to obtain powder 10.

Synthesis Example 11

Copper Molybdenum Oxysulfide ($Cu_xMo_yO_zS_\gamma$) Powder 11

4.6 grams of copper nitrate ($Cu(NO_3)_2.2.5H_2O$) is dissolved in 250 mL of distilled water to obtain a first solution. 3.0 grams of molybdenum (V) chloride ($MoCl_5$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 95° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol.

The precipitate is dried by an evaporator to obtain powder 11.

Synthesis Example 12

Copper Silver Oxysulfide ($Cu_xAg_yO_zS_\gamma$) Powder 12

4.6 grams of copper nitrate ($Cu(NO_3)_2.2.5H_2O$) is dissolved in 250 mL of distilled water to obtain a first solution. 3.0 grams of silver (I) nitrate ($AgNO_3$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 80° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 12.

$CO_2$ Reduction Reaction

Example 1

$CO_2$ Reduction Reaction for Methanol Using Catalyst Powder 1

The catalytic reduction of $CO_2$ is conducted in a quartz glass reactor. 0.1 grams of the catalyst powder 1 and 100 mL of distilled water are added to the reactor and are being stirred with a magnet with a stirring speed of 280 rpm (revolutions per minute). Subsequently, $CO_2$ gas is passed into the reactor. The $CO_2$ gas is generated by decomposing sodium bicarbonate ($NaHCO_3$) with the addition of diluted nitric acid ($HNO_3$) aqueous solution (V:V) in a dropwise manner. The $CO_2$ gas is allowed to react with the distilled water for 16-24 or t hours, depending upon the rate of $NaHCO_3$ consumption. The volume $V_1$ (unit: mL) of excessive amount of the non-reacted $CO_2$ passed into the reactor is measured by collecting gas over water displacement method. In other words, the volume of non-reacted $CO_2$ in the reactor during the duration of the reaction time of t hours is denoted by $V_1$. After the reaction time of t hours, the remaining $NaHCO_3$ is continued to be decomposed by the addition of $HNO_3$, and the volume $V_2$ (unit: mL) of $CO_2$ gas generated herein is measured by collecting gas over water displacement method. Another trial of decomposing $NaHCO_3$ without the presence of the catalyst is performed, and the volume of $CO_2$ generated is denoted by $V_0$. Specifically, in the present embodiment, 5.0 grams of $NaHCO_3$ has been decomposed and 1295 mL of $CO_2$ is obtained. In other words, $V_0$ is a constant value of 1295 mL in the present embodiment.

The volume $V_3$ of $CO_2$ gas being converted with the aid of the catalyst may be calculated by the following formula:

$$V_3 = V_0 - V_1 - V_2.$$

The volume $V_3$ of CO2 converting into methanol can be calculated in terms of reaction rate with the unit of mmol/g·h by the following formula:

$$R(mmol/g \cdot h) = \frac{(V_3/1000)}{22.4 \times m \times t}$$

R is the methanol generation rate, t is the reaction time (unit: hour), m is the amount of catalyst used (unit: g), and 22.4 L/mole is the molar volume of ideal gas at STP condition.

It should be noted that no other organic compounds except for methanol is detected in the solution. Moreover, the procedure of Example 1 has been conducted thrice. The first trial and the second trial are conducted with the presence of ambient light. The third trial is conducted in a dark room. In other words, no external energy is present in the third trial. The amount of methanol obtained in Example 1 is illustrated in Table 1 below.

Examples 2-8

$CO_2$ Reduction Reaction for Methanol Using Catalyst Powders 2-8

Similar procedures as that of Example 1 have been conducted except the catalyst powder 1 is replaced by catalyst powders 2-8 respectively in Examples 2-8 and the procedures of some Examples have not been conducted for the second/third trials. It should be noted that Example 2-8 are only performed at a condition in which ambient light is present. The amount of methanol obtained in Examples 2-8 are summarized in Table 1 below.

Example 9

$CO_2$ Reduction Reaction for Methanol Using the Recycled Catalyst Powder 1 after the First Trial Similar procedure as that of Example 1 for powder 1 under the ambient light has been conducted for the recycled powder 1 after the first trial. The amount of methanol obtained in Example 9 are summarized in Table 1 below.

Comparative Example 1

$CO_2$ Reduction Reaction for Methanol Using Catalyst Powder Having a Chemical Formula of $CuO_zS_\gamma$ Similar procedure as that of Example 1 has been conducted except the catalyst powder 1 is replaced by catalyst powder having a chemical formula of $CuO_zS_\gamma$ without the second metal $M^{(2)}$ from its precursor. The amount of methanol obtained in Comparative Example 1 is summarized in Table 1 below.

TABLE 1

| | Catalyst | $CH_3OH$ rate for first trial in ambient light (mmol/g · h) | $CH_3OH$ rate for second trial in ambient light (mmol/g · h) | $CH_3OH$ rate for third trial in dark room (mmol/g · h) | $CH_3OH$ rate for the used catalyst in ambient light (mmol/g · h) |
|---|---|---|---|---|---|
| Example 1 | $Cu_xZn_yO_zS_\gamma$ | 25.95 (25.57)* | 24.00 | 13.20 (13.00)* | — |
| Example 2 | $Cu_xMn_yO_zS_\gamma$ | 18.68 (18.90)* | 15.66 | — | — |
| Example 3 | $Cu_xCo_yO_zS_\gamma$ | 16.74 (16.77)* | 15.92 | — | — |

TABLE 1-continued

| | Catalyst | $CH_3OH$ rate for first trial in ambient light (mmol/g·h) | $CH_3OH$ rate for second trial in ambient light (mmol/g·h) | $CH_3OH$ rate for third trial in dark room (mmol/g·h) | $CH_3OH$ rate for the used catalyst in ambient light (mmol/g·h) |
|---|---|---|---|---|---|
| Example 4 | $Cu_xNi_yO_zS_\gamma$ | 14.56 (14.26)* | 15.16 | — | — |
| Example 5 | $Cu_xIn_yO_zS_\gamma$ | 12.97 (13.27)* | 12.28 | — | — |
| Example 6 | $Cu_xSn^{II}{}_yO_zS_\gamma$ | 29.02 (29.31)* | 29.21 | — | — |
| Example 7 | $Cu_xCe_yO_zS_\gamma$ | 12.60 (12.48)* | — | — | — |
| Example 8 | $Cu_xSb_yO_zS_\gamma$ | 11.52 (11.79)* | — | — | — |
| Example 9 | $Cu_xZn_yO_zS_\gamma$ | — | — | — | 22.95 |
| Comparative Example 1 | $CuO_zS_\gamma$ | 0 | — | — | — |

* The values in brackets are the methanol generation rate obtained by GC-FID.

The numerical value of methanol obtained in Table 1 is the amount of methanol obtained per hour per gram of catalyst powder used. As clearly illustrated in Table 1, the bimetal oxysulfide solid-solution catalyst of the invention is able to aid the conversion of $CO_2$ gas to methanol under atmospheric condition or in a dark room. As such, the power requirement for external energy may be eliminated. In addition, as the reduction duration lasting for 16-24 hours, the second trials with the new catalyst has the similar methanol generation rate to the first one. Moreover, as clearly illustrated in Example 9, the methanol generation rate obtained by recycling used bimetal oxysulfide solid-solution catalyst is still decent, thereby proving the reusability of the bimetal oxysulfide solid-solution catalyst of the invention. Therefore, the cost of the reduction process may be significantly lowered.

In order to verify the volume $V_3$ of $CO_2$ gas is converted to methanol, the following verification procedure is performed on the mixture solution.

Verification Method 1: Gas Chromatography-Flame Ionization Detector (GC-FID)

A GC-FID detector is being used to measure the methanol concentration in the mixture solution for the methanol generation rate. The testing condition is as follows:

HP-INNDWAX capillary column: 30 m×0.25 mm
Device: FID detector
Inlet temperature: 200° C.
Split ratio: 100:1
Sample volume: 2 μL
Column oven temperature: 180° C.
Detector temperature: 200° C.
Flow rate of hydrogen gas: 35 mL/min
Flow rate of air: 400 mL/min
Flow rate of high purity $N_2$ assist gas: 30 mL/min.

The methanol generation rates were confirmed by GC-FID detector for Examples 1-8 in the ambient light and for Example 1 in the dark room. The data were shown in the brackets in Table 1 and matches with the results obtained from the $CO_2$ volume conversion.

Verification Method 2: Spectrophotometer

Alternatively, a spectrophotometry may also be adapted to verify the existence of methanol in the mixture solution. An UV-VIS Spectrophotometer manufactured by Shimadzu Scientific Instruments has been used. The reagents are formulated by the following methods.

Potassium permanganate-phosphoric acid solution: dissolving 3 grams of potassium permanganate ($KMnO_4$) in 15 mL of 85% phosphoric acid ($H_3PO_4$, Analytical reagent AR level) solution and 70 mL of distilled water. Subsequently, additional distilled water is added to obtain a total volume of 100 mL and the solution is mixed uniformly.

Oxalic acid-sulfuric acid solution: dissolving 7 grams of oxalic acid ($H_2C_2O_4.2H_2O$, AR level) in 100 mL of 1:1 (V:V) cold sulfuric acid.

Fuchsine-sulfurous acid solution: dissolving 0.1 grams of basic fuchsine (AR level) in 60 mL of hot water having a temperature of approximately 80° C. After the solution is cooled, 10 mL of 10% sodium sulfite ($Na_2SO_3$, AR level) and 1 mL of concentrated hydrochloric acid (HCl) are added to the solution. The solution is stirred and water is added to obtain a total volume of 100 mL. The solution is mixed uniformly and is stored in a brown bottle for at least 2 hours until the solution appears to be colorless.

Methanol standard solution: accurately drawing 1.000 gram of absolute methanol and placing the absolute methanol to form a 1000 mL solution in a flask. Water is added until the tick mark is reached. Shake the solution to ensure uniform mixing. The solution contains 1 g/L of methanol and is stored at a low temperature.

The testing method is as follows: accurately taking x mL of sample. (5.0–x) mL of water and 2.0 mL potassium permanganate-phosphoric acid solution are added to the sample. After the solution is placed for 15 minutes, 0.6 mL of oxalic acid-sulfuric acid solution is added to the solution to allow the color of the solution to fade. Subsequently, 5.0 mL of fuchsine-sulfurous acid solution is added. After the solution is mixed uniformly and placed for 30 minutes, the absorbance of the solution at a wavelength of 545 nm is measured by the spectrophotometer. Based on the absorbance measured, the methanol content may be inferred from a standard curve and the concentration of the methanol in the solution may be calculated.

The result obtained by spectrophotometer matches the result illustrated in Table 1.

Based on the verification methods above, it is apparent that the bimetal oxysulfide solid-solution catalyst of the invention is able to aid the conversion of $CO_2$ to methanol. In other words, by using the bimetal oxysulfide solid-solution catalyst of the invention, undesired $CO_2$ gas can be easily converted to useful fuel sources without the presence of external energy. Therefore, the reduction of $CO_2$ gas may be achieved at a lower cost.

Heavy Metal Reduction Reaction

Example 1

Hexavalent Chromium (Cr(VI)) Reduction Reaction Using Catalyst Powder 1

0.1 grams of the catalyst powder 1 is placed in a 250 mL conical flask. Subsequently, 100 mL of hexavalent chromium (Cr(VI)) aqueous solution with a concentration of 50 ppm is added into the conical flask. Thereafter, shake the conical flask to render a uniform distribution of the catalyst powder 1 in the hexavalent chromium aqueous solution. The catalyst powder 1 and the hexavalent chromium aqueous solution are allowed to react for 2 minutes. Subsequently, a sample of 2 mL of the solution is filter by a syringe filter. The absorbance of the sample is measured by UV-VIS spectrophotometer and the concentration of the hexavalent chromium in the sample is calculated according to Lambert-Beer Law.

The foregoing process may be repeated with the catalyst powder 1 being recycled. In detail, the catalyst powder 1 may be centrifuged to separate from the solution. Without rinsing the catalyst powder 1, the foregoing process is repeated for 6 times.

The removal rate of hexavalent chromium in the solution is illustrated in Table 2 below. It should be noted that the removal rate of the hexavalent chromium may be calculated by comparing the original hexavalent chromium concentration and the remaining hexavalent chromium concentration after the heavy metal reduction reaction.

Examples 2-7

Hexavalent Chromium (Cr(VI)) Reduction Reaction Using Catalyst Powders 2-6, 11

Similar procedure as that of Example 1 has been conducted except the catalyst powder 1 is replaced by catalyst powders 2-6 respectively in Examples 2-6, and by catalyst powder 11 in Example 7. The removal rates of hexavalent chromium in the solution are summarized in Table 2 below.

TABLE 2

| Catalyst | | First Trial (%) | Second Trial (%) | Third Trial (%) | Fourth Trial (%) | Fifth Trial (%) | Sixth Trial (%) |
|---|---|---|---|---|---|---|---|
| Example 1 | $Cu_xZn_yO_zS_\gamma$ | 100 | 100 | 100 | 97.8 | 94.1 | 82.9 |
| Example 2 | $Cu_xMn_yO_zS_\gamma$ | 100 | 100 | 100 | 100 | 97.2 | 94.6 |
| Example 3 | $Cu_xCo_yO_zS_\gamma$ | 100 | 100 | 100 | 100 | 97.2 | 93.8 |
| Example 4 | $Cu_xNi_yO_zS_\gamma$ | 100 | 100 | 100 | 97.7 | 96.9 | 95.0 |
| Example 5 | $Cu_xIn_yO_zS_\gamma$ | 100 | 100 | 97.6 | 96.0 | 93.3 | 90.5 |
| Example 6 | $Cu_xSn^{II}_yO_zS_\gamma$ | 100 | 100 | 96.9 | 95.1 | 94.1 | 84.4 |
| Example 7 | $Cu_xMo_yO_zS_\gamma$ | 100 | 99.3 | 98.7 | 95.6 | 91.1 | — |

Examples 8-12

Hexavalent Chromium (Cr(VI)) Reduction Reaction Using Catalyst Powders 7-10 and 12

Similar procedure as that of Example 1 has been conducted except the catalyst powder 1 is replaced by catalyst powders 7-10 respectively in Examples 8-11, and by catalyst powder 12 in Example 12 and the hexavalent chromium aqueous solutions are allowed to react for 60 minutes. The removal rates of hexavalent chromium in the solution are 18% for Example 8 ($Cu_xCe_yO_zS_\gamma$), 38.5% for Example 9 ($Cu_xSb_yO_zS_\gamma$), 32.2% for Example 10 ($Cu_xGa_yO_zS_\gamma$), 85.7% for Example 11 ($Cu_xSn^{IV}_yO_zS_\gamma$), and 5.3% for Example 12 ($Cu_xAg_yO_zS_\gamma$).

It is commonly known that hexavalent chromium is highly toxic. As clearly illustrated in Table 2, the catalyst of the invention is able to aid the elimination of hexavalent chromium under atmospheric condition in a fast rate. 0.1 g of the catalyst is able to remove 0.03 g Cr(VI) in a short period and is still available. The resulting solution may be recycled for other use without causing damage to human body. In addition, as illustrated in Table 2, when the catalyst is recycled, the ability of aiding the conversion is not compromised. Therefore, the cost for the reduction processes may be significantly lowered.

Hydrogenation Reaction of Organic Compounds

Example 1 (RhB)

Rhodamine B Hydrogenation Reaction Using Catalyst Powder 1

50 mL of Rhodamine B aqueous solution (a dye solution) with a concentration of 20 ppm is add into a 100 mL conical flask. Subsequently, 5 mL of sodium boron hydride aqueous solution with a concentration of 0.1 mole is added into the conical flask. Under the stirring condition, 0.01 grams of catalyst powder 1 is provided in the conical flask. The catalyst powder 1 and the Rhodamine B aqueous solution are allowed to react. Subsequently, a sample of 2 mL of the solution is taken out after the dye colour change into colourless and filter by a syringe filter. The absorbance of the filtered solution is measured by UV-VIS spectrophotometer and the dye concentration in the sample is calculated according to Lambert-Beer Law.

The time required for the complete hydrogenation reaction of Rhodamine B in the solution is illustrated in Table 3 below. It should be noted that the complete reduction of the Rhodamine B may be calculated by comparing the original Rhodamine B concentration without the addition of sodium boron hydride and the remaining dye concentration after the hydrogenation reduction reaction.

Examples 2-12 (RhB)

Rhodamine B Hydrogenation Reactions Using Catalyst Powders 2-12

Similar procedure as that of Example 1 (RhB) has been conducted except the catalyst powder 1 is replaced by catalyst powders 2-12 respectively in Examples 2-12 (RhB). The times required for the complete hydrogenation reaction of Rhodamine B in the solution are summarized in Table 3 below.

Examples 1-12 (MO)

Methyl Orange Hydrogenation Reactions Using Catalyst Powders 1-12

Similar procedure as that of Example 1 (RhB) has been conducted for catalyst powders 1-12 respectively in Examples 1-12 (MO) except for Rhodamine B changed to methyl orange. The times required for the complete hydrogenation reaction of methyl orange in the solution are summarized in Table 3 below.

Examples 1-12 (MB)

Methylene Blue Hydrogenation Reactions Using Catalyst Powders 1-12

Similar procedure as that of Example 1 (RhB) has been conducted for catalyst powders 1-12 respectively in Examples 1-12 (MB) except for Rhodamine B changed to methylene blue and its dye solution changed to 100 mL of methylene blue aqueous solution with a concentration of 100 ppm in a 250 mL conical flask. The times required for the complete hydrogenation reaction of methylene blue in the solution are summarized in Table 3 below.

Comparative Example 1 (RhB)

Rhodamine B Hydrogenation Reactions Using Catalyst $CuO_zS_\gamma$

Similar procedure as that of Example 1 (RhB) has been conducted. The times required for the complete hydrogenation reaction of Rhodamine B in the solution are summarized in Table 3 below.

Comparative Example 1 (MO)

Methyl Orange Hydrogenation Reactions Using Catalyst $CuO_zS_\gamma$

Similar procedure as that of Example 1 (MO) has been conducted. The times required for the complete hydrogenation reaction of methyl orange in the solution are summarized in Table 3 below.

Comparative Example 1 (MB)

Methylene Blue Hydrogenation Reactions Using Catalyst $CuO_zS_\gamma$

Similar procedure as that of Example 1 (MB) has been conducted. The times required for the complete hydrogenation reaction of methylene blue in the solution are summarized in Table 3 below.

TABLE 3

| Catalyst | | Time for completing hydrogenation of Rhodamine B (RhB) (minute) | Time for completing hydrogenation of Methyl orange (MO) (minute) | Time for completing hydrogenation of Methylene blue (MB) (minute) |
| --- | --- | --- | --- | --- |
| Example 1 | $Cu_xZn_yO_zS_\gamma$ | 1 | slow | 3 |
| Example 2 | $Cu_xMn_yO_zS_\gamma$ | 2 | 3 | 5 |
| Example 3 | $Cu_xCo_yO_zS_\gamma$ | 2 | 1 | 3 |
| Example 4 | $Cu_xNi_yO_zS_\gamma$ | 1 | 1 | 4 |
| Example 5 | $Cu_xIn_yO_zS_\gamma$ | 2 | slow | 4 |
| Example 6 | $Cu_xSn^{II}_yO_zS_\gamma$ | 1 | 2 | 3 |
| Example 7 | $Cu_xCe_yO_zS_\gamma$ | 2 | slow | 2 |
| Example 8 | $Cu_xSb_yO_zS_\gamma$ | slow | 4 | 6 |
| Example 9 | $Cu_xGa_yO_zS_\gamma$ | 2 | slow | 8 |
| Example 10 | $Cu_xSn^{IV}_yO_zS_\gamma$ | 2 | slow | 13 |
| Example 11 | $Cu_xMo_yO_zS_\gamma$ | slow | 1 | 3 |
| Example 12 | $Cu_xAg_yO_zS_\gamma$ | No reaction | No reaction | No reaction |
| Comparative Example 1 | $CuO_zS_\gamma$ | 2 | 3 | 3 |

The hydrogenation reactions of rhodamine B, methyl orange, and methylene blue under catalyst involve the C—N=C bonding in molecules changed to C—NH—C. $Cu_xSn^{II}_yO_zS_\gamma$ performs the best in all three different organic molecules. These hydrogenation reactions at the ambient condition involve the green chemical processes, which can be beneficial for the industry, biology, and pharmacy.

Based on the foregoing, the bimetal oxysulfide solid-solution catalyst in the invention includes several advantages. For example, the bimetal oxysulfide solid-solution catalyst may be manufactured at a low temperature, thereby ensure safety in the manufacturing process. Moreover, due to the specific structure and composition of the bimetal oxysulfide solid-solution catalyst of the invention, reduction of $CO_2$ gas, reduction of heavy metal, and the hydrogenation of organic compounds may be performed at atmospheric condition. As such, the power requirement for external energy may be eliminated. In addition, the bimetal oxysulfide solid-solution catalyst of the invention may be recycled for repeated uses. Therefore, the cost for the reduction processes may be significantly lowered.

It will be apparent to those skilled in the art that various modifications and variations can be made to the structure and composition of the present invention without departing from the scope or spirit of the invention. In view of the foregoing, it is intended that the present invention covers modifications and variations of this invention provided they fall within the scope of the following claims and their equivalents.

What is claimed is:

1. A bimetal oxysulfide solid-solution catalyst represented by the following formula:

$$Cu_xM^{(2)}_yO_zS_\gamma,$$

wherein $M^{(2)}$ comprises a mono-, di-, tri-, tetra-, or penta-valent metal; $0<y<0.3$; $0.7<x<1.0$; $0<z<0.5$; $0.5<\gamma<1.0$.

2. The bimetal oxysulfide solid-solution catalyst according to claim 1, $M^{(2)}$ comprises monovalent Silver (Ag), divalent Zinc (Zn), Manganese (Mn), Nickel (Ni), Cobalt (Co), and Tin ($Sn^{II}$), trivalent Indium (In), Cerium (Ce), Antimony (Sb), and Gallium (Ga), tetravalent Tin ($Sn^{IV}$), or pentavalent Molybdenum (Mo).

3. A manufacturing method of the bimetal oxysulfide solid-solution catalyst according to claim 1, comprising:
 dissolving a copper-containing salt in distilled water to obtain a first solution;
 dissolving an $M^{(2)}$-containing compound in distilled water to obtain a second solution;
 mixing the first solution and the second solution to obtain a mixture solution;
 adding an organosulfur compound into the mixture solution;

heating the mixture solution to a temperature range of 50-100° C.;

centrifuging for precipitate from the mixture solution;

drying the precipitate, so as to obtain the catalyst.

4. The manufacturing method of the bimetal oxysulfide solid-solution catalyst according to claim 3, further comprising:

adding hydrazine to the mixture solution in a dropwise manner.

5. A method for carbon dioxide ($CO_2$) reduction, comprising:

providing the bimetal oxysulfide solid-solution catalyst according to claim 1 in a reactor;

adding a reactant solution in the reactor; and passing $CO_2$ gas into the reactor to react with the reactant solution.

6. The method for carbon dioxide reduction according to claim 5, wherein the reactant solution comprises water.

7. A method for heavy metal reduction, comprising:

providing the bimetal oxysulfide solid-solution catalyst according to claim 1 in a reactor;

adding a heavy metal aqueous solution in the reactor; and reacting the bimetal oxysulfide solid-solution catalyst and the heavy metal aqueous solution.

8. The method for heavy metal reduction according to claim 7, wherein the heavy metal comprises hexavalent chromium (Cr(VI)).

9. A method for hydrogenation of organic compounds, comprising:

providing the bimetal oxysulfide solid-solution catalyst according to claim 1 in a reactor;

adding an aqueous solution of organic compounds and a reducing agent in the reactor; and reacting the bimetal oxysulfide solid-solution catalyst and the organic aqueous solution.

10. The method for hydrogenation of organic compounds according to claim 9, wherein the organic compounds comprise rhodamine B, methyl orange, or methylene blue.

11. The method of hydrogenation of organic compounds according to claim 9, wherein the reducing agent comprises sodium boron hydride or oxalic acid.

* * * * *